United States Patent
Miura

(10) Patent No.: US 10,713,627 B2
(45) Date of Patent: Jul. 14, 2020

(54) ENDOSCOPIC SCOPE CLEANING MANAGEMENT SYSTEM, ENDOSCOPIC SCOPE CLEANING MANAGEMENT METHOD, AND NON-TRANSITORY COMPUTER READABLE MEDIUM

(71) Applicant: FUJIFILM Corporation, Tokyo (JP)

(72) Inventor: Goro Miura, Kanagawa (JP)

(73) Assignee: FUJIFILM CORPORATION, Tokyo (JP)

(*) Notice: Subject to any disclaimer, the term of this patent is extended or adjusted under 35 U.S.C. 154(b) by 592 days.

(21) Appl. No.: 14/674,553

(22) Filed: Mar. 31, 2015

(65) Prior Publication Data

US 2015/0278460 A1 Oct. 1, 2015

(30) Foreign Application Priority Data

Mar. 31, 2014 (JP) ................. 2014-074480

(51) Int. Cl.
*G06Q 10/00* (2012.01)
*A61B 1/00* (2006.01)
(Continued)

(52) U.S. Cl.
CPC ......... *G06Q 10/20* (2013.01); *A61B 1/00059* (2013.01); *A61B 1/121* (2013.01);
(Continued)

(58) Field of Classification Search
CPC ... G06F 19/327; A61B 1/00059; A61B 1/121; G16H 40/20; G16H 40/40
(Continued)

(56) References Cited

U.S. PATENT DOCUMENTS

2001/0041825 A1 11/2001 Shibata et al.
2004/0049172 A1* 3/2004 Root ................. A61B 1/00016
606/1
(Continued)

FOREIGN PATENT DOCUMENTS

EP 1864607 A2 * 12/2007 ......... A61B 1/00006
JP 2002-028132 A 1/2002
(Continued)

OTHER PUBLICATIONS

Japanese Office Action dated Apr. 12, 2016 with an English translation thereof.
(Continued)

*Primary Examiner* — Hiep V Nguyen
(74) *Attorney, Agent, or Firm* — McGinn I.P. Law Group, PLLC

(57) ABSTRACT

An endoscopic scope cleaning management system includes: an inspection order information storage unit which stores inspection order information including information of inspection date and time of an endoscope inspection using an endoscopic scope; an endoscopic scope specification unit which specifies an endoscopic scope to be used based on the inspection order information stored in the inspection order information storage unit; a cleaning necessity determination unit which stores cleaning history information of each endoscopic scope and determines whether it is necessary to clean the endoscopic scope to be used which is specified by the endoscopic scope specification unit, using the cleaning history information of the endoscopic scope to be used; and an information creation unit which creates and outputs information for notifying a user of the necessity to clean a cleaning-needed endoscopic scope for which it is determined by the cleaning necessity determination unit that the cleaning is required.

16 Claims, 5 Drawing Sheets

| NO. | NAME OF PATIENT | INSPECTION DATE AND TIME | DOCTOR IN CHARGE | INSPECTION CLASSIFICATION | SCOPE TO BE USED | DESIGNATED SCOPE |
|---|---|---|---|---|---|---|
| 1 | a | 20yy/mm/dd 9:00 | A | UPPER ENDOSCOPE INSPECTION | SCOPE FOR UPPER PART | |
| 2 | b | 20yy/mm/dd 9:00 | C | UPPER ENDOSCOPE INSPECTION | SCOPE FOR UPPER PART | SCOPE A4 |
| 3 | c | 20yy/mm/dd 10:00 | A | UPPER ENDOSCOPE INSPECTION | SCOPE FOR UPPER PART | |
| 4 | d | 20yy/mm/dd 11:00 | B | LOWER ENDOSCOPE INSPECTION | SCOPE FOR LOWER PART | |
| 5 | e | 20yy/mm/dd 13:00 | B | LOWER ENDOSCOPE INSPECTION | SCOPE FOR LOWER PART | |
| 6 | f | 20yy/mm/dd 15:00 | B | LOWER ENDOSCOPE INSPECTION | SCOPE FOR LOWER PART | |

(51) Int. Cl.
*A61B 1/12* (2006.01)
*G06Q 10/08* (2012.01)
*G16H 40/20* (2018.01)

(52) U.S. Cl.
CPC ............ *A61B 1/123* (2013.01); *G06Q 10/087* (2013.01); *G16H 40/20* (2018.01)

(58) Field of Classification Search
USPC .............................................................. 705/2
See application file for complete search history.

(56) References Cited

U.S. PATENT DOCUMENTS

| | | |
|---|---|---|
| 2008/0162184 A1 | 7/2008 | Matsubara et al. |
| 2009/0055215 A1* | 2/2009 | Giraldo ............... G06Q 10/087 705/2 |
| 2009/0103836 A1 | 4/2009 | Shimizu et al. |
| 2009/0206674 A1 | 8/2009 | Noguchi et al. |
| 2010/0030573 A1* | 2/2010 | Araki ................. G06Q 10/087 705/2 |
| 2010/0268545 A1 | 10/2010 | Inaba et al. |
| 2014/0326282 A1* | 11/2014 | Kawachi ................ A61B 19/34 134/99.1 |

FOREIGN PATENT DOCUMENTS

| | | |
|---|---|---|
| JP | 2002-282200 A | 10/2002 |
| JP | 2007-050240 A | 3/2007 |
| JP | 2008-054861 A | 3/2008 |
| JP | 2008-117382 A | 5/2008 |
| JP | 2009-095502 A | 5/2009 |
| JP | 2010-039560 A | 2/2010 |
| JP | 2010-088720 A | 4/2010 |
| JP | 4616933 B2 | 1/2011 |
| JP | 2012-164285 A | 8/2012 |
| JP | 2013-116234 A | 6/2013 |

OTHER PUBLICATIONS

Extended European Search Report dated Aug. 6, 2015.
Communication pursuant to Article 94(3) EPC in European Application No. 15 161 660.4 dated Sep. 5, 2017.

* cited by examiner

FIG. 2

| NO. | NAME OF PATIENT | INSPECTION DATE AND TIME | DOCTOR IN CHARGE | INSPECTION CLASSIFICATION | SCOPE TO BE USED | DESIGNATED SCOPE |
|---|---|---|---|---|---|---|
| 1 | a | 20yy/mm/dd 9:00 | A | UPPER ENDOSCOPE INSPECTION | SCOPE FOR UPPER PART | |
| 2 | b | 20yy/mm/dd 9:00 | C | UPPER ENDOSCOPE INSPECTION | SCOPE FOR UPPER PART | SCOPE A4 |
| 3 | c | 20yy/mm/dd 10:00 | A | UPPER ENDOSCOPE INSPECTION | SCOPE FOR UPPER PART | |
| 4 | d | 20yy/mm/dd 11:00 | B | LOWER ENDOSCOPE INSPECTION | SCOPE FOR LOWER PART | |
| 5 | e | 20yy/mm/dd 13:00 | B | LOWER ENDOSCOPE INSPECTION | SCOPE FOR LOWER PART | |
| 6 | f | 20yy/mm/dd 15:00 | B | LOWER ENDOSCOPE INSPECTION | SCOPE FOR LOWER PART | |

FIG. 3

| SCOPE ID | FINAL CLEANING DATE AND TIME | | TO BE USED | CLEANING-NEEDED |
|---|---|---|---|---|
| SCOPE A1 | YESTERDAY | 11:00 | O | O |
| SCOPE A2 | DAY BEFORE YESTERDAY | 7:00 | O | O |
| SCOPE A3 | YESTERDAY | 12:00 | | O |
| SCOPE A4 | YESTERDAY | 13:00 | O | O |
| SCOPE B1 | YESTERDAY | 14:00 | O | O |
| SCOPE B2 | YESTERDAY | 18:00 | O | |
| SCOPE B3 | YESTERDAY | 15:00 | O | O |
| SCOPE B4 | YESTERDAY | 19:00 | | |

FIG. 4

| SCOPE ID | STATUS | FINAL CLEANING DATE AND TIME | | CLEANING-NEEDED |
|---|---|---|---|---|
| SCOPE A2 | IN-STORAGE | DAY BEFORE YESTERDAY | 7:00 | O |
| SCOPE A1 | IN-STORAGE | YESTERDAY | 11:00 | O |
| SCOPE A4 | IN-STORAGE | YESTERDAY | 13:00 | O |
| SCOPE B1 | IN-STORAGE | YESTERDAY | 14:00 | O |
| SCOPE B3 | IN-STORAGE | YESTERDAY | 15:00 | O |
| SCOPE B2 | IN-STORAGE | YESTERDAY | 18:00 | |
| SCOPE A3 | IN-STORAGE | YESTERDAY | 12:00 | O |

FIG. 5

| SCOPE ID | STATUS | FINAL CLEANING DATE AND TIME | | CLEANING-NEEDED |
|---|---|---|---|---|
| SCOPE A4 | IN-STORAGE | YESTERDAY | 13:00 | O |
| SCOPE A2 | IN-STORAGE | DAY BEFORE YESTERDAY | 7:00 | O |
| SCOPE A1 | IN-STORAGE | YESTERDAY | 11:00 | O |
| SCOPE B1 | IN-STORAGE | YESTERDAY | 14:00 | O |
| SCOPE B3 | IN-STORAGE | YESTERDAY | 15:00 | O |
| SCOPE B2 | IN-STORAGE | YESTERDAY | 18:00 | |
| SCOPE A3 | IN-STORAGE | YESTERDAY | 12:00 | O |

ENDOSCOPIC SCOPE CLEANING MANAGEMENT SYSTEM, ENDOSCOPIC SCOPE CLEANING MANAGEMENT METHOD, AND NON-TRANSITORY COMPUTER READABLE MEDIUM

CROSS-REFERENCE TO RELATED APPLICATIONS

This application is based on and claims priority under 35 USC 119 from Japanese Patent Application No. 2014-074480 filed on Mar. 31, 2014, the entire content of which is incorporated herein by reference.

BACKGROUND

1. Technical Field

The present invention relates to an endoscopic scope cleaning management system, an endoscopic scope cleaning management method, and a non-transitory computer readable medium.

2. Related Art

An endoscopic scope used in an inspection is cleaned. The endoscopic scope which has been subjected to cleaning treatment is typically hygienically managed by being stored in a storage warehouse except for a case of being immediately used in a next inspection. Moreover, a system which supports storage management of the endoscopic scope is known (for example, refer to Patent Literature 1 (JP-A-2002-282200), Patent Literature 2 (JP-A-2008-54861), and Patent Literature 3 (JP-A-2009-95502)).

In a storage management system of an endoscope disclosed in Patent Literature 1, when an endoscopic scope is stored in a storage warehouse, the storage warehouse communicates with the endoscopic scope to read out a model name of the endoscope or data relating to cleaning, which has been stored in the endoscopic scope and to display the model name or a cleaning state.

In an endoscope storage warehouse disclosed in Patent Literature 2, the time elapsed since an endoscopic scope is stored in the storage warehouse is measured. In a case where a predetermined storage restriction period has elapsed, a lamp indicating that the endoscopic scope is unusable is lighted. If the period is within the storage restriction period, a lamp indicating that the endoscopic scope is usable is lighted.

In an endoscope information management system disclosed in Patent Literature 3, cleaning history information of an endoscopic scope is transmitted from a cleaning device to a server to unitarily manage the condition of cleaning of an individual endoscopic scope through the server.

SUMMARY OF INVENTION

In the systems disclosed in Patent Literatures 1 to 3, it is easy to grasp the condition of an individual endoscopic scope, but determination of whether it is necessary to clean an endoscopic scope to be used in relationship with an inspection is not performed. For this reason, there is a possibility that a situation may occur in which the necessity to clean the endoscopic scope is determined in a stage where the endoscopic scope is to be used.

In view of above, an object of the present invention is to provide an endoscopic scope cleaning management system, an endoscopic scope cleaning management method, and the like which enable performing highly efficient inspection.

(1) An aspect the present invention provides an endoscopic scope cleaning management system comprising: an inspection order information storage unit which stores inspection order information including information of inspection date and time of an endoscope inspection using an endoscopic scope; an endoscopic scope specification unit which specifies an endoscopic scope to be used based on the inspection order information stored in the inspection order information storage unit; a cleaning necessity determination unit which stores cleaning history information of each endoscopic scope and determines whether it is necessary to clean the endoscopic scope to be used which is specified by the endoscopic scope specification unit, using the cleaning history information of the endoscopic scope to be used; and an information creation unit which creates and outputs information for notifying a user of the necessity to clean a cleaning-needed endoscopic scope for which it is determined by the cleaning necessity determination unit that the cleaning is required.

(2) Another aspect of the present invention provides an endoscopic scope cleaning management method comprising: specifying an endoscopic scope to be used based on inspection order information including information of inspection date and time of an endoscope inspection using the endoscopic scope; determining whether it is necessary to clean the endoscopic scope to be used, using cleaning history information of the specified endoscopic scope to be used; and creating and outputting information for notifying a user of a necessity to clean a cleaning-needed endoscopic scope for which it is determined that the cleaning is required.

(3) Another aspect of the present invention provides a program causing a computer to execute a process of the endoscopic scope cleaning management method according to (2).

According to any one of the aspects of the present invention, it is possible to provide the endoscopic scope cleaning management system and the endoscopic scope cleaning management method which enable performing highly efficient inspection.

BRIEF DESCRIPTION OF DRAWINGS

FIG. 2 is a view showing an example of inspection order information.

FIG. 3 is a view showing an example of specifying an endoscopic scope to be used, and determining whether it is necessary to clean the endoscopic scope.

FIG. 4 is a view showing an example of information for notifying a user of the necessity to clean a cleaning-needed endoscopic scope.

FIG. 5 is a view showing another example of information for notifying a user of the necessity to clean a cleaning-needed endoscopic scope.

DESCRIPTION OF EMBODIMENTS

Figure 1:
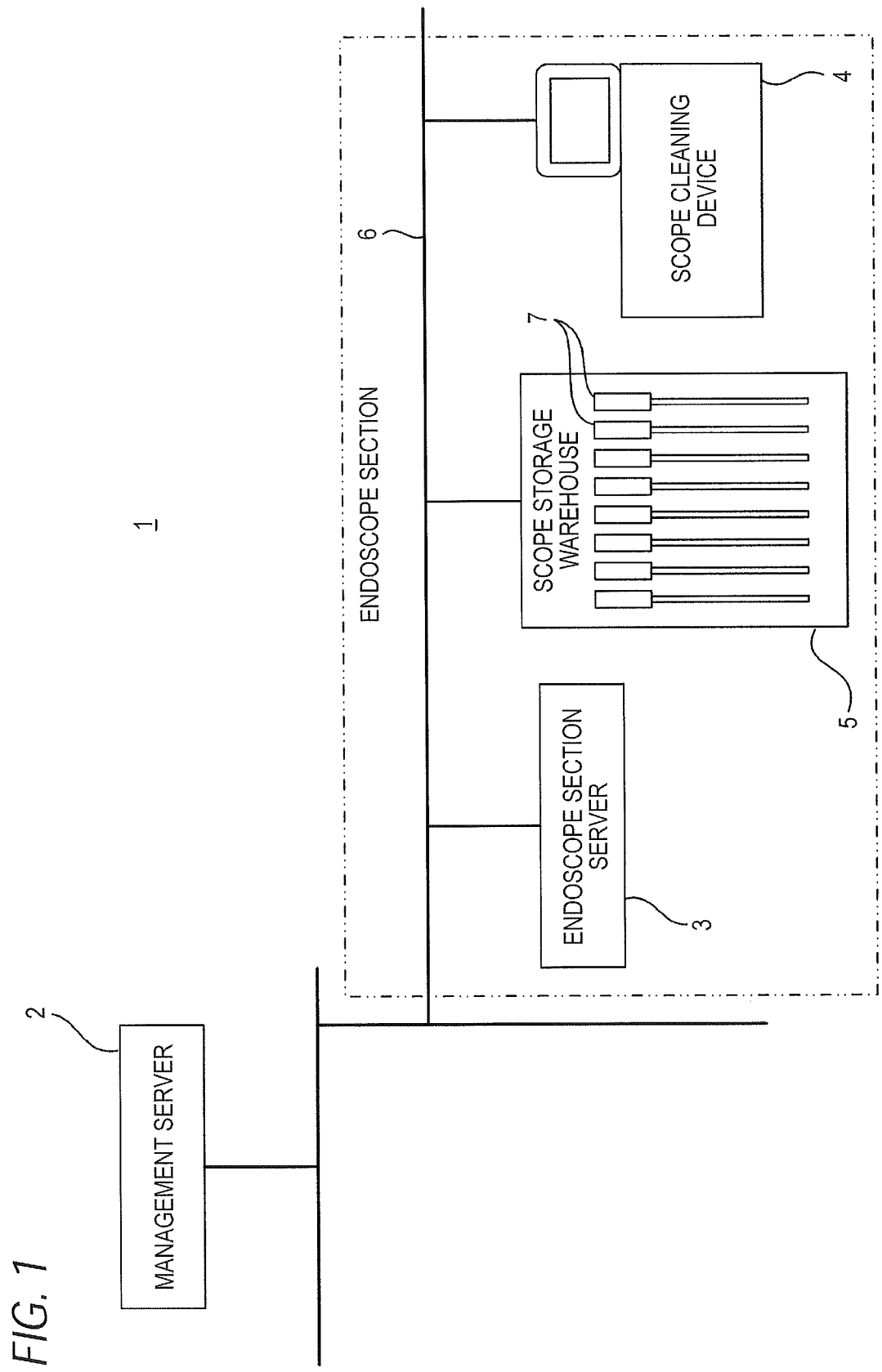
FIG. 1 is a view, for describing an embodiment of the present invention, which shows a configuration of an example of an endoscopic scope cleaning management system.

Hereinafter, a preferred embodiment of the present invention will be described with respect to the accompanying drawings.

FIG. 1 shows a configuration of an example of an endoscopic scope cleaning management system for describing an embodiment of the present invention.

An endoscopic scope cleaning management system 1 shown in FIG. 1 includes a management server 2, an endoscope section server 3, a scope cleaning device 4, and a scope storage warehouse 5. The management server 2, the endoscope section server 3, the scope cleaning device 4, and the scope storage warehouse 5 are communicatively connected to each other through a network 6 such as a local area network (LAN).

The management server 2 stores a reservation for medical examination, an inspection order, and an electronic medical chart. For example, when an inspection order with respect to an endoscopic section is issued from another section, information regarding the inspection order is transmitted to the endoscope section through the management server 2.

Examples of inspection order information with respect to the endoscope includes a name of a patient, inspection date and time, a doctor in charge, an inspection classification (for example, upper endoscopy or lower endoscopy), the type of scope to be used (for example, a scope for an upper part or a scope for a lower part), and the like. In general, in the inspection order, only the type of the endoscopic scope is designated, but it is also possible to designate an individual endoscopic scope. For example, there is a difference in operability for each individual even in the same type of the endoscopic scope, and therefore, in some cases, an individual endoscopic scope is designated in terms of preference or familiarity with respect to the difference between individuals depending on doctors. In this case, information for designating an individual endoscopic scope is also included in the inspection order information.

The endoscope section server 3 is installed in the endoscopic section and performs an inspection in the endoscopic scope and management of an endoscopic scope 7.

The scope cleaning device 4 carries out cleaning treatment with respect to a used endoscopic scope 7 to make the endoscopic scope 7 reusable.

In addition, the scope cleaning device 4 records history information regarding cleaning treatment of the endoscopic scope 7. For example, identification information is added to the endoscopic scope 7, and the scope cleaning device 4 is provided with means for acquiring the identification information of the endoscopic scope 7. Examples of the identification information of the endoscopic scope 7 and means for acquiring the same include a bar code and a bar code reader.

The scope cleaning device 4 acquires identification information from the endoscopic scope 7 and transmits status information of the endoscopic scope 7 during cleaning to the endoscope section server 3. In addition, after completion of the cleaning treatment, the scope cleaning device 4 records cleaning history information of the endoscopic scope 7 in association with the identification information acquired from the endoscopic scope 7 and information regarding the cleaning treatment applied to the endoscopic scope 7, and transmits the cleaning history information to the endoscope section server 3. The cleaning history information includes, for example, the date and time when the cleaning treatment is carried out, the content of the treatment, and the like.

The scope storage warehouse 5 stores the endoscopic scope 7 which is subjected to cleaning treatment using the scope cleaning device 4. The scope storage warehouse 5 is also provided with means for acquiring identification information of the endoscopic scope 7 similarly to the scope cleaning device 4, and transmits status information of in-storage or in-delivery regarding each endoscopic scope 7 which is stored in the scope storage warehouse 5, to the endoscope section server 3.

The endoscope section server 3 stores the cleaning history information of the endoscopic scope 7 which is transmitted from the scope cleaning device 4. The endoscope section server 3 creates a cleaning schedule of the endoscopic scope 7 based on the inspection order information transmitted from the management server 2 and the cleaning history information stored in the endoscope section server 3.

FIG. 2 shows an example of inspection order information which is transmitted from the management server 2 to the endoscope section server 3.

The cleaning schedule of the endoscopic scope can be created at an arbitrary time width, and the time width of the cleaning schedule is, for example, one day or an AM-PM half day. The time width of the cleaning schedule is designated by, for example, a user of the endoscopic scope cleaning management system 1. Hereinafter, description will be made by setting the time width of the cleaning schedule to one day.

For example, when inspection work in the endoscopic section is started, inspection order information for one day is transmitted from the management server 2 to the endoscope section server 3. Then, the endoscope section server 3 specifies an endoscopic scope to be used today based on the inspection order information acquired from the management server 2.

Here, a valid period during which the degree of hygiene is maintained is set for cleaning treatment of an endoscopic scope, and cleaning treatment is carried out on an endoscopic scope of which the valid period is expired even if the endoscopic scope has not been used.

The endoscope section server 3 determines the types or the required number of endoscopic scopes corresponding to the inspection classification such as upper endoscopy or lower endoscopy based on the inspection order information and selects an endoscopic scope to be used in order from the longest elapsed time from the final cleaning date and time based on cleaning history information of each endoscopic scope to specify an endoscopic scope to be used.

In addition, as shown in the example of the drawing, in a case where the inspection order information includes information of designating an individual endoscopic scope (endoscopic scope A4), the endoscope section server 3 specifies an endoscopic scope to be used including the designated endoscopic scope.

Next, the endoscope section server 3 determines whether it is necessary to clean each endoscopic scope to be used, using cleaning history information of each endoscopic scope to be used. Examples of criteria of a case where it is determined that cleaning of the endoscopic scope is required include the following (A) to (C).

(A) Case where remaining period of above-described valid period is less than predetermined threshold value Th1
(B) Case where end of above-described valid period is today
(C) Case where elapsed time from final cleaning treatment exceeds predetermined threshold value TH2

Then, the endoscope section server 3 creates and outputs information for notifying a user of the necessity to clean the endoscope for which it has been determined that the cleaning is required.

In the endoscopic scope cleaning management system 1, the management server 2 functions as an inspection order information storage unit which stores inspection order information including information of inspection date and time of an endoscope inspection using an endoscopic scope; and the endoscope section server 3 functions as an endoscopic scope specification unit which specifies an endoscopic scope to be used, a cleaning necessity determination unit which determines whether it is necessary to clean an endoscopic scope to be used, and an information creation unit which creates and outputs information for notifying a user of the necessity to clean a cleaning-needed endoscopic scope for which it has been determined that the cleaning is required.

FIG. 3 shows an example of specifying an endoscopic scope to be used, and determining whether it is necessary to clean the endoscopic scope. FIG. 4 shows an example of information for notifying a user of the necessity to clean a cleaning-needed endoscopic scope.

Hereinafter, it is set such that the cleaning schedule is created at a point of time of 8:00 when inspection work in the endoscopic section is started. In addition, the above-described valid period is 48 hours, the threshold value TH1 which is set for a remaining period for the valid period is 12 hours, and the threshold value TH2 which is set for an elapsed time from final cleaning treatment is 15 hours.

An endoscopic scope to be used is specified from endoscopic scopes A1 to A4 for an upper endoscope inspection and endoscopic scopes B1 to B4 for a lower endoscope inspection by the endoscope section server 3 based on the inspection order information shown in FIG. 2.

The inspection order information shown in FIG. 2 includes information of designating the endoscopic scope A4 as an endoscopic scope to be used in the upper endoscope inspection, and therefore, the endoscopic scope A4 is first selected. Then, endoscopic scopes A1 and A2 are selected in order from the longest elapsed time from the final cleaning date and time as described above. Similarly, endoscopic scopes B1, B2, and B3 are selected with respect to the lower endoscope inspection. Accordingly, endoscopic scopes to be used are specified.

Then, it is determined whether it is necessary to clean the endoscopic scopes A1, A2, A4, B1, B2, and B3 to be used by the endoscope section server 3 using the cleaning history information, according to the determination criteria of the above-described (A) to (C).

In regard to the endoscopic scope B2, at the time point of 8:00 am, the remaining period of the valid period is longer than or equal to 12 hours which is set as a predetermined threshold value TH1, the end of the valid period is tomorrow, and the elapsed time from the final cleaning treatment is shorter than or equal to 15 hours which is set as a predetermined threshold value TH2, and therefore, it is determined that cleaning is not required. In regard to other endoscopic scopes A1, A2, A4, B1, and B3, it is determined that cleaning is required since they correspond to at least one of the criteria of the above-described (A) to (C).

Then, the endoscope section server 3 creates a list of endoscopic scopes A1, A2, A4, B1, B2, and B3 to be used as information for notifying a user of the necessity to clean the cleaning-needed endoscopic scopes A1, A2, A4, B1, and B3 for which it has been determined that cleaning is required. Among these, in regard to the cleaning-needed endoscopic scopes A1, A2, A4, B1, and B3, an index "O" indicating that cleaning is required is added to the column of "cleaning-needed" of the list, and this index is displayed on a monitor of the endoscope section server 3. An endoscopic scope (endoscopic scope A3 in the example in the drawing) which corresponds to at least one of the determination criteria of the above-described (A) to (C) but is not included in the endoscopic scope to be used may also be included in the cleaning-needed endoscopic scope and added to the above-described list.

Here, it is preferable that the cleaning treatment is carried out in order from the longest elapsed time from the final cleaning date and time. The endoscope section server 3 designates the order of cleaning treatment by sorting the time in order from the longest elapsed time from the final cleaning date and time based on the cleaning history information in the above-described list. In a case where the endoscopic scope (endoscopic scope A3 in the example in the drawing) not to be used in the above-described list is included, cleaning treatment of the endoscopic scope to be used is prioritized and the order of cleaning treatment of the endoscopic scope not to be used may be set to be after the endoscopic scope to be used regardless of the elapsed time from the final cleaning date and time. A user performs cleaning treatment of the endoscopic scope in accordance with the order designated in the list which is shown in the monitor. Notification for prompting cleaning in accordance with the cleaning schedule may be performed in addition to the display of the list.

The display of the column of "status" of the list is updated by status information of the endoscopic scope which is transmitted from the scope cleaning device 4 and the scope storage warehouse 5 to the endoscope section server 3. In addition, the display of the columns of "final cleaning date and time" and "cleaning-needed" of the list is updated by the cleaning history information of the endoscopic scope transmitted from the scope cleaning device 4 to the endoscope section server 3. By referring to the list, it is possible to grasp the degree of congestion of the scope cleaning device 4 and to approximately grasp the required time until cleaning treatment of each endoscopic scope is finished.

In this example in which information for designating the endoscopic scope A4 is included in the inspection order, as shown in FIG. 5, the order of the cleaning treatment of the designated endoscopic scope A4 may be set to be earlier than that of other cleaning-needed endoscopic scopes A1, A2, B1, and B3 which are not designated regardless of the elapsed time from the final cleaning date and time. In a case of setting the order of the cleaning treatment of the designated endoscopic scope A4 to be earlier, for example, the order of the cleaning treatment of the designated endoscopic scope A4 may be made earlier than that of all of other cleaning-needed endoscopic scopes regardless of the type of the endoscopic scope; or the order of the cleaning treatment of the designated endoscopic scope A4 may be set to be in order from the longest elapsed time from the final cleaning date and time between cleaning-needed endoscopic scopes (endoscopic scopes B1 and B3 in this example) of the different types among the cleaning-needed endoscopic scopes by being set to be earlier than those of cleaning-needed endoscopic scopes (endoscopic scopes A1 and A2 in this example) of the same types among the cleaning-needed endoscopic scopes.

In addition, it has been described in the above-described example that the valid period during which the degree of hygiene is maintained is set in the same manner regardless of the classification or the individual of the endoscopic scope. However, the above-described valid period may vary depending on the classification or the individual of the endoscopic scope, and in this case, the threshold value TH1 which is set for the remaining period of the above-described valid period or the threshold value TH2 which is set for the elapsed time from the final cleaning treatment may also vary depending on the classification or the individual of the endoscopic scope.

According to the endoscopic scope cleaning management system 1, it is possible to avoid a situation in which the necessity to clean an endoscopic scope is determined in a stage where the endoscopic scope is to be used and to perform highly efficient inspection, by determining whether it is necessary to clean the endoscopic scope to be used in relationship with an inspection.

It is also possible to provide an endoscopic scope cleaning management method which is performed by the above-described endoscopic scope cleaning management system 1 as a program. In such a program, the program is recorded in a computer-readable non-temporary (non-transitory) recording medium. Such a "computer-readable recording medium" includes, for example, an optical medium such as a Compact Disc-ROM (CD-ROM); or a magnetic recording medium such as a memory card. In addition, such a program can be provided by being downloaded through a network. The above-described program is utilized by, for example, being installed in the endoscope section server 3 and provides a function of performing cleaning management of an endoscopic scope.

Hereinabove, the following matter is disclosed in the present specification as described above.

(1) It is an endoscopic scope cleaning management system including: an inspection order information storage unit which stores inspection order information including information of inspection date and time of an endoscope inspection using an endoscopic scope; an endoscopic scope specification unit which specifies an endoscopic scope to be used based on the inspection order information stored in the inspection order information storage unit; a cleaning necessity determination unit which stores cleaning history information of each endoscopic scope and determines whether it is necessary to clean the endoscopic scope to be used which is specified by the endoscopic scope specification unit, using the cleaning history information of the endoscopic scope to be used; and an information creation unit which creates and outputs information for notifying a user of the necessity to clean a cleaning-needed endoscopic scope for which it is determined by the cleaning necessity determination unit that the cleaning is required.

(2) The endoscopic scope cleaning management system according to (1), may have a configuration in which the information creation unit creates and outputs information for designating an order of cleaning of the cleaning-needed endoscopic scope based on the cleaning history information of the cleaning-needed endoscopic scope.

(3) The endoscopic scope cleaning management system according to (2), may have a configuration in which in a case where information for designating an individual endoscopic scope is included in the inspection order information and the designated endoscopic scope is included in the cleaning-needed endoscopic scopes, the information creation unit makes the order to clean the designated endoscopic scope earlier than that of other cleaning-needed endoscopic scopes.

(4) An endoscopic scope cleaning management method including: specifying an endoscopic scope to be used based on inspection order information including information of inspection date and time of an endoscope inspection using the endoscopic scope; determining whether it is necessary to clean the endoscopic scope to be used, using cleaning history information of the specified endoscopic scope to be used; and creating and outputting information for notifying a user of a necessity to clean a cleaning-needed endoscopic scope for which it is determined that the cleaning is required.

(5) The endoscopic scope cleaning management method according to (4), may have a configuration in which information for designating an order of cleaning of the cleaning-needed endoscopic scope based on the cleaning history information of the cleaning-needed endoscopic scope is created and output.

(6) The endoscopic scope cleaning management method according to (5), may have a configuration in which in a case where information for designating an individual endoscopic scope is included in the inspection order information and the designated endoscopic scope is included in the cleaning-needed endoscopic scopes, the order to clean the designated endoscopic scope is made to be earlier than that of other cleaning-needed endoscopic scopes.

(7) It is a program causing a computer to execute a process of the endoscopic scope cleaning management method according to any one of (4) to (6).

What is claimed is:

1. An endoscopic scope cleaning management system comprising:
   a storage which stores inspection order information including information of an inspection date and time of an endoscope inspection using an endoscopic scope;
   a processor coupled to the storage, the processor being configured to:
   specify an endoscopic scope to be used based on the inspection order information stored in the storage;
   store cleaning history information associated with identification information of the endoscopic scope and information regarding a cleaning treatment applied to the endoscopic scope, and determine whether it is necessary to clean the endoscopic scope to be used which is specified, using the cleaning history information of the endoscopic scope to be used; and
   create a cleaning schedule of the endoscopic scope based on the inspection order information, based on the cleaning schedule of the endoscopic scope, the creating of the cleaning schedule including creating and outputting information for notifying a user of a necessity to clean a cleaning-needed endoscopic scope for which it is determine that the cleaning is required; and
   a scanner that reads the identification information of the endoscopic scope,
   wherein criteria where the processor determines that cleaning of the endoscopic scope is required include:
      when a remaining period of a valid period of the endoscopic scope to be used is less than a first predetermined threshold value, the valid period is set for the cleaning treatment of the endoscopic scope;
      when an end of the valid period is a current day; and
      when an elapsed time from a final cleaning treatment to the endoscopic scope to be used exceeds a second predetermined threshold value,
   wherein the processor creates and outputs information for designating a sequential order of cleaning of the cleaning-needed endoscopic scope based on the cleaning history information of the cleaning-needed endoscopic scope, and
   wherein the processor creates the cleaning schedule of the endoscopic scope such that the cleaning treatment of the endoscopic scope is carried out in a descending order of an elapsed time from the final cleaning treatment.

2. The endoscopic scope cleaning management system according to claim 1, wherein, when information for designating an individual endoscopic scope is included in the inspection order information and the designated endoscopic scope is included in the cleaning-needed endoscopic scopes, the processor makes an order to clean the designated endoscopic scope earlier than that of other cleaning-needed endoscopic scopes.

3. The endoscopic scope cleaning management system according to claim 1, wherein the first predetermined threshold value is different from the second predetermined threshold value.

4. The endoscopic scope cleaning management system according to claim 1, wherein the endoscopic scope cleaning management system further comprises a monitor, and information indicating that cleaning is required is displayed on the monitor.

5. The endoscopic scope cleaning management system according to claim 1, wherein the processor determines whether it is necessary to clean the endoscopic scope to be used, using the cleaning history information transmitted from a scope cleaning device for cleaning the endoscopic scope.

6. The endoscopic scope cleaning management system according to claim 5, wherein the scope cleaning device is connected to the endoscopic scope cleaning management system through a network.

7. The endoscopic scope cleaning management system according to claim 1, wherein the information regarding the cleaning treatment includes a date and a time of the cleaning treatment.

8. The endoscopic scope cleaning management system according to claim 1, wherein the information regarding the cleaning treatment includes information on a treatment that is previously applied to the endoscopic scope.

9. The endoscopic scope cleaning management system according to claim 1, wherein the processor specifies the endoscopic scope to be used in the descending order of the elapsed time from the final cleaning treatment.

10. An endoscopic scope cleaning management method, comprising:
    specifying, by a processor, an endoscopic scope to be used based on inspection order information including information of an inspection date and a time of an endoscope inspection using the endoscopic scope;
    determining, by the processor, whether it is necessary to clean the endoscopic scope to be used, using cleaning history information associated with identification information of the endoscopic scope and information regarding a cleaning treatment applied to the endoscopic scope;
    creating, by processor, a cleaning schedule of the endoscopic scope based on the inspection order information;
    creating and outputting, by the processor, based on the cleaning schedule of the endoscopic scope, information for notifying a user of a necessity to clean a cleaning-needed endoscopic scope for which it is determined that the cleaning is required; and
    scanning the identification information of the endoscopic scope,
    wherein criteria where it is determined that cleaning of the endoscopic scope is required include:
        when a remaining period of a valid period of the endoscopic scope to be used is less than a first predetermined threshold value, the valid period is set for the cleaning treatment of the endoscopic scope;
        when an end of the valid period is a current day; and
        when an elapsed time from a final cleaning treatment to the endoscopic scope to be used exceeds a second predetermined threshold value,
    wherein information for designating a sequential order of cleaning of the cleaning-needed endoscopic scope based on the cleaning history information of the cleaning-needed endoscopic scope is created and is output, and
    wherein the processor creates the cleaning schedule of the endoscopic scope such that the cleaning treatment of the endoscopic scope is carried out in a descending order of an elapsed time from the final cleaning treatment.

11. The endoscopic scope cleaning management method according to claim 10, wherein, when information for designating an individual endoscopic scope is included in the inspection order information and the designated endoscopic scope is included in the cleaning-needed endoscopic scopes, an order to clean the designated endoscopic scope is made to be earlier than that of other cleaning-needed endoscopic scopes.

12. The endoscopic scope cleaning management method according to claim 10, wherein the information regarding the cleaning treatment includes a date and a time of the cleaning treatment.

13. The endoscopic scope cleaning management method according to claim 10, wherein the information regarding the cleaning treatment includes information on a treatment that is previously applied to the endoscopic scope.

14. The endoscopic scope cleaning management method according to claim 10, wherein the processor specifies the endoscopic scope to be used in the descending order of the elapsed time from the final cleaning treatment.

15. A non-transitory computer readable medium storing a program causing a computer to execute:
    specifying, by a processor, an endoscopic scope to be used based on inspection order information including information of an inspection date and a time of an endoscope inspection using the endoscopic scope;
    determining, by the processor, whether it is necessary to clean the endoscopic scope to be used, using cleaning history information associated with identification information of the endoscopic scope and information regarding a cleaning treatment applied to the endoscopic scope;
    creating, by the processor, a cleaning schedule of the endoscopic scope based on the inspection order information;
    creating and outputting, by the processor, based on the cleaning schedule of the endoscopic scope, information for notifying a user of a necessity to clean a cleaning-needed endoscopic scope for which it is determined that the cleaning is required; and
    scanning the identification information of the endoscopic scope,
    wherein criteria where it is determined that cleaning of the endoscopic scope is required include:
        when a remaining period of a valid period of the endoscopic scope to be used is less than a first predetermined threshold value, the valid period is set for the cleaning treatment of the endoscopic scope;
        when an end of the valid period is a current day; and
        when an elapsed time from a final cleaning treatment to the endoscopic scope to be used exceeds a second predetermined threshold value,
    wherein information for designating a sequential order of cleaning of the cleaning-needed endoscopic scope based on the cleaning history information of the cleaning-needed endoscopic scope is created and is output, and
    wherein the processor creates the cleaning schedule of the endoscopic scope such that the cleaning treatment of the endoscopic scope is carried out in a descending order of an elapsed time from the final cleaning treatment.

16. The non-transitory computer readable medium according to claim 15, wherein the processor specifies the endoscopic scope to be used in the descending order of the elapsed time from the final cleaning treatment.

* * * * *